United States Patent
Nielson

(10) Patent No.: US 6,723,067 B2
(45) Date of Patent: Apr. 20, 2004

(54) APPARATUS FOR DELIVERING AEROSOLIZED FIBRIN ENDOSCOPICALLY TO A WOUND

(76) Inventor: David H. Nielson, 1411 Greystone Ridge, San Antonio, TX (US) 78258

( * ) Notice: Subject to any disclaimer, the term of this patent is extended or adjusted under 35 U.S.C. 154(b) by 428 days.

(21) Appl. No.: 09/915,878

(22) Filed: Jul. 26, 2001

(65) Prior Publication Data

US 2003/0023202 A1 Jan. 30, 2003

(51) Int. Cl.$^7$ .......................... A61M 37/00; A61M 5/00; B67D 5/52; B67D 5/60
(52) U.S. Cl. .......................... 604/82; 604/191; 222/135; 222/145.4; 222/145.5
(58) Field of Search .......................... 604/27, 36, 38, 604/46, 48, 82, 93.01, 181, 187, 191, 218, 240, 241, 242, 243, 264, 275, 284, 533, 534, 535; 222/135, 137, 145.1, 145.4, 145.5

(56) References Cited

U.S. PATENT DOCUMENTS

| | | |
|---|---|---|
| 2,112,160 A | 3/1938 | Johnson |
| 2,533,004 A | 12/1950 | Ferry et al. |
| 3,467,096 A | 9/1969 | Horn |
| 3,552,394 A | 1/1971 | Horn |
| 3,767,085 A | 10/1973 | Cannon et al. |
| 3,828,980 A | 8/1974 | Creighton et al. |
| 4,040,420 A | 8/1977 | Speer |
| 4,329,988 A | 5/1982 | Sarnoff et al. |
| 4,359,049 A | 11/1982 | Redl et al. |
| 4,610,666 A | 9/1986 | Pizzino |
| 4,631,055 A | 12/1986 | Redl et al. |
| 4,673,395 A | 6/1987 | Phillips |
| 4,735,616 A | 4/1988 | Eibl et al. |
| 4,740,203 A | 4/1988 | Hoskins et al. |
| 5,104,375 A | 4/1992 | Wolf et al. |
| 5,116,315 A | 5/1992 | Capozzi et al. |
| 5,226,877 A | 7/1993 | Epstein |
| 5,320,639 A | 6/1994 | Rudnick |
| 5,322,510 A | 6/1994 | Lindner et al. |
| 5,443,481 A | 8/1995 | Lee |
| 5,935,437 A * | 8/1999 | Whitmore ................. 210/321.6 |
| 5,989,215 A * | 11/1999 | Delmotte et al. ............. 604/82 |
| 6,059,749 A * | 5/2000 | Marx ........................... 604/82 |
| 6,454,739 B1 * | 9/2002 | Chang ......................... 604/82 |
| 6,461,325 B1 * | 10/2002 | Delmotte et al. ............. 604/82 |

* cited by examiner

Primary Examiner—Manuel Mendez
Assistant Examiner—Mark K. Han
(74) Attorney, Agent, or Firm—Michelle Evans; Gunn & Lee, P.C.

(57) ABSTRACT

An apparatus for delivering aerosolized fibrin endoscopically to a wound is disclosed. The apparatus has a pair of syringes for holding fibrin precursors, a mixing chamber for mixing the fibrin precursors separately with pressurized gas to form individual aerosol solutions, and a delivery tube for delivery of the aerosol solutions to a remote surgical site for formation of an aerosolized fibrin seal.

4 Claims, 1 Drawing Sheet

APPARATUS FOR DELIVERING AEROSOLIZED FIBRIN ENDOSCOPICALLY TO A WOUND

BACKGROUND OF THE INVENTION

1. Field of the Invention

Applicant's invention relates to an apparatus for delivering a biocompatible adhesive, more particularly aerosolized fibrin, endoscopically to a wound.

2. Background Information

Endoscopy is a surgical technique that involves the use of an endoscope, a special viewing instrument that allows a surgeon to see images of the body's internal structure through very small incisions. The endoscope itself consists of two basic parts. The first is a tubular probe fitted with a tiny camera and a bright light which is inserted through the small incision and the second is a viewing screen which magnifies the transmitted images of the body's internal structures from the camera. During surgery, the surgeon watches the screen while moving the tube of the endoscope through the surgical area. The endoscope functions as a viewing device only. To perform the surgery, a separate surgical instrument, such as a scalpel, scissors, or forceps, must be inserted through a different point of entry and manipulated within the tissue.

In a typical endoscopic procedure only a few small incisions, each preferably less than one inch long, are needed to insert the endoscope tube and other instruments. Since the incisions are shorter with endoscopy, the risk of sensory loss from nerve damage is decreased. Also, bleeding, bruising and swelling may be significantly reduced.

However, with these advantages it is still necessary, as with traditional long incision surgery, that a fibrin glue be used at the surgical site to hold the tissue together for healing promoting hemostasis and sealing of air leaks. Fibrin in the human body is the product of an activated coagulation system. It is an insoluble protein formed in the extravascular space from fibrinogen by the proteolytic action of thrombin during the normal clotting of blood.

Fibrin glue delivery systems that mimic this natural body process exist for traditional long incision surgery. Typically in these systems, the thrombin and fibrinogen are kept in separate containers. When the fibrin glue seal is needed to seal a surgical site, preferably equally amounts of the fibrinogen and thrombin are combined and the enzymatic action of the thrombin on the fibrinogen forms the fibrin. The reaction is nearly instantaneous. Due to the reaction kinetics, both the delivery and mixing of the precursor fibrin components to the wound or surgical site must occur rapidly and accurately before the reaction occurs to form the fibrin.

This rapid rate of reactivity to form the fibrin does not typically present difficulties when applied to traditional long incision surgery, but does present a problem in endoscopic surgeries. Sealing a surgical site with a fibrin glue after endoscopic surgery requires delivering the fibrin endoscopically through a small surgical incision, over an enclosed distance underneath the skin, for ultimate delivery to a remote surgical site. Unfortunately, none of the existing fibrin delivery systems appear to be able to accommodate delivery of aerosolized fibrin endoscopically to a remote surgical site. Aerosolized fibrin mixes the two components (thrombin and fibrinogen) more effectively than existing endoscopic delivery systems. The more effective the mixing, the more effective the glue (sealing action). The present invention was designed to satisfy this long felt need of a more effective (fibrin) biologic sealant in endoscopic surgery.

SUMMARY OF THE INVENTION

It is an object of the present invention to provide a novel apparatus for delivering aerosolized fibrin endoscopically to a wound.

It is another object of the present invention to provide a novel apparatus for delivering aerosolized fibrin endoscopically to a wound having a novel mixing chamber.

Yet another object of the present invention is to provide a novel apparatus for delivering fibrin endoscopically to a wound that incorporates a carrier gas ($CO_2$ or nitrogen, etc.) to convert the fibrin precursor solutions into aerosolized solutions which are mixed more efficiently and create a more effective sealant.

Another object of the present invention is to provide a novel apparatus for delivering fibrin endoscopically to a wound that incorporates a specialized mixing chamber for the carrier gas with the separate fibrin precursors.

It is another object of the present invention to provide a novel apparatus for delivering fibrin endoscopically to a wound that permits a surgeon to introduce an aerosolized fibrin seal into a remote endoscopic surgical site.

Still another object of the present invention is to provide a novel apparatus for delivering fibrin endoscopically to a wound that alleviates the risk of the aerosolized fibrin precursors reacting prematurely to form fibrin while still within the delivery tube which would clog the tube.

An additional object of the present invention is to provide a novel apparatus for delivering aerosolized fibrin endoscopically to a wound that carries the fibrin precursor solutions through the delivery tube before they react to form fibrin.

In satisfaction of these and related objectives, Applicant's present invention provides for an apparatus for delivering aerosolized fibrin endoscopically to a wound. Applicant's invention permits its practitioner to introduce an aerosolized fibrin seal into a remote endoscopic surgical site without the risk of the fibrin precursors combining prematurely within the the delivery tube. Aerosolization provides for better mixing of the fibrin precursors (thrombin and fibrinogen) which creates more effective fibrin for sealing air leaks and hemostatis.

DETAILED DESCRIPTION OF THE PREFERRED EMBODIMENT

Figure 1:
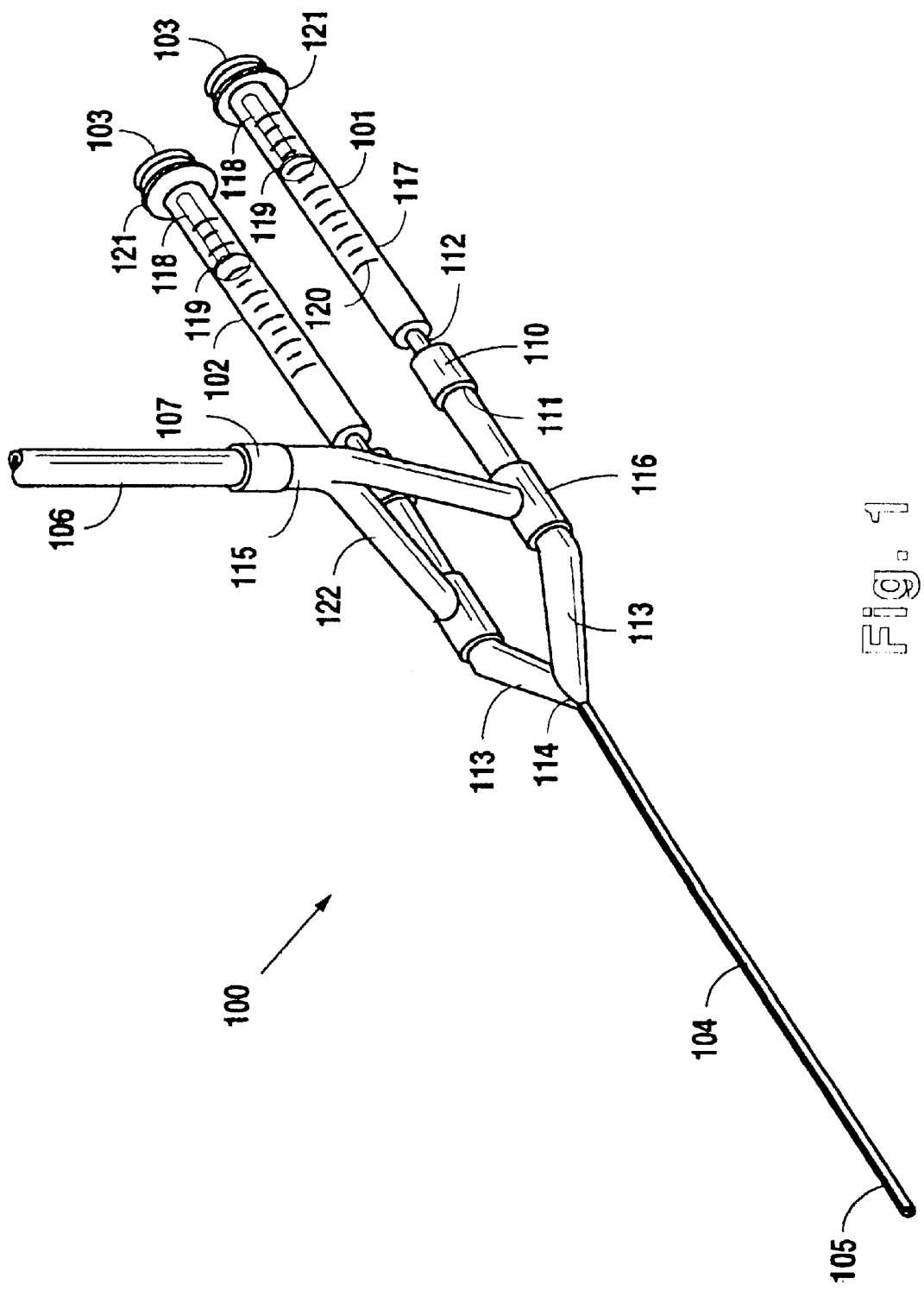
FIG. 1 is a perspective view of the preferred embodiment of the present invention.

Referring to FIG. 1, a perspective view of the preferred embodiment of the present invention is shown. The delivery apparatus 100 has two syringes 101 and 102 for accommodating the fibrin precursors thrombin and fibrinogen, respectively. The syringes 101 and 102 are placed at a variable distance apart. Each syringe 101 and 102 has a cylindrical body 117 with a nozzle 112 at one end and an open base at the other end accommodating a radial extension 121. Along the length of cylindrical body 117 are graduations 120 to indicate the amount of the respective fibrin precursors introduced into the syringes 101 and 102. Through the open base of the cylindrical body 117 is inserted a plunger 118 having a compressor 119 at one end and a finger engager 103 at the opposite end. The plunger 118 is slidingly engaged within the cylindrical body 117 in such a way that the outer surface of compressor 119 remains in contact with the inner surface of the cylindrical body 117. The syringes 101 and 102 can be made of any suitable medical grade material and can be of any size consistent with the necessary application. The plunger 118 is preferably made of a medical grade elastic material such as rubber.

The open end of nozzle 112 of both syringes 101 and 102 is situated within and forms a fluid tight connection with one end of first collars 110. The opposite end of first collars 110 joins with a fluid tight connection to one end of necks 111 which feed with a fluid tight connection into one end of mixing chambers 116. First collars 110, necks 111, and mixing chambers 116 can be made of any suitable medical grade material and can be of any size consistent with the application.

Tubes 113 join with a fluid tight connection from the opposite end of mixing chambers 116 into a first Y-junction 114. First Y-junction 114 terminates in a dual lumen delivery tube 104 having a release nozzle 105 at its opposite end. The dimensions of delivery tube 104 can vary based the application. Tubes 113, first Y-junction 114, and delivery tube 104 are constructed of a suitable medical grade material.

Up from the top of mixing chambers 116 are one end of arms 122. Arms 122 terminate in a second Y-junction 115 which connects with a fluid and gas tight connection into third collar 107 at one end. Third collar 107 has dimensions that vary based on the application. A tube 106 is placed within third collar 107 at its opposite end with a fluid and gas tight connection. A source of high pressure gas (nitrogen or carbon dioxide) (not shown) can be connected to the mixing chambers 116 by way of tube 106.

In operating the fibrin delivery apparatus of the present invention, an amount of fibrinogen solution is filled in one syringe 101 and an equal amount of the thrombin solution is filled in the second syringe 102. The finger engagers 103 of the syringes 101 and 102 are depressed which allows the compressors 119 to exert pressure on the respective fibrin precursor solutions within the syringes 101 and 102 forcing the solutions out through the respective nozzles 112 through first collars 110 and into mixing chamber 116. At least one unidirectional valve may be placed between the nozzles 112 and the mixing chambers 116 to prevent retrograde flow of the solutions back in to the syringes 101 and 102. Coincident with this process, nitrogen or carbon dioxide gas from a remote source (not shown) is introduced through tube 106, past third collar 107, through arms 122 into mixing chambers 116 containing the respective solutions. At least one unidirectional valve may be placed between the remote source of gas and the mixing chambers 116 to prevent retrograde flow of the solutions back into the remote source. Placement of the arms 122 at between a 45 degree and 90 degree angle from second Y junction 115 may tend to minimize any retrograde flow into the remote source of gas.

The high pressure of the gas mixes the gas into the respective solutions aerosolizing them and converting them into separate high pressure aerosols. The high pressure aerosols pass rapidly out of mixing chambers 116 into tubes 113 and past the first Y junction 114 into the dual lumen delivery tube 104 where both aerosol solutions are carried separately then mixed as they exit the tip.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A fibrin delivery system for delivering aerosolized fibrin endoscopically to a remote surgical site where the fibrin precursors must be kept separate from each other until they reach the remote surgical site, said fibrin delivery system comprising:

a first syringe cylindrical body for storing a first fibrin precursor component and a second syringe cylindrical body for storing a second fibrin precursor component;

a separate compressor attached to a plunger associated with each of said syringe cylindrical bodies for expelling from each of said syringe cylindrical bodies its associated fibrin precursor component;

a separate mixing chamber attached to each of said syringe cylindrical bodies for receiving said expelled fibrin precursor components and for mixing said fibrin precursor components with pressurized gas to form separate aerosolized fibrin precursor components; and a delivery tube attached to each mixing chamber for receiving each of said aerosolized fibrin precursor components and delivering said aerosolized fibrin precursor components to said remote surgical site whereby upon mixing of the two aerosolized fibrin precursor components and stabilization by each of said aerosolized fibrin precursor components said fibrin is formed.

2. The fibrin delivery system for delivering aerosolized fibrin endoscopically to a remote surgical site of claim 1 further comprising a source of pressurized gas associated with said mixing chamber.

3. The fibrin delivery system for delivering aerosolized fibrin endoscopically to a remote surgical site of claim 2 further comprising a first Y-junction connecting said mixing chamber and said delivery tube.

4. The fibrin delivery system for delivering aerosolized fibrin endoscopically to a remote surgical site of claim 3 further comprising a second Y-junction connecting said mixing chamber and said source of pressurized gas.

* * * * *